US008765904B2

(12) United States Patent
Amey

(10) Patent No.: US 8,765,904 B2
(45) Date of Patent: Jul. 1, 2014

(54) POLYETHERAMINES, COMPOSITIONS INCLUDING POLYETHERAMINES, AND METHODS OF MAKING

(75) Inventor: Ronald L. Amey, Wilmington, DE (US)

(73) Assignee: INVISTA North America S.à r.l., Wilmington, DE (US)

(*) Notice: Subject to any disclaimer, the term of this patent is extended or adjusted under 35 U.S.C. 154(b) by 235 days.

(21) Appl. No.: 13/230,145

(22) Filed: Sep. 12, 2011

(65) Prior Publication Data
US 2012/0065362 A1 Mar. 15, 2012

Related U.S. Application Data

(60) Provisional application No. 61/381,453, filed on Sep. 10, 2010.

(51) Int. Cl.
C08G 59/18 (2006.01)
C08G 59/20 (2006.01)
C08G 59/00 (2006.01)
C08G 65/00 (2006.01)

(52) U.S. Cl.
USPC ........ 528/417; 528/422; 528/425; 528/502 R; 525/242; 525/330.9; 525/331.1

(58) Field of Classification Search
USPC ............ 525/242, 330.9, 331.1; 528/417, 425, 528/502 R, 422
See application file for complete search history.

(56) References Cited

U.S. PATENT DOCUMENTS

| 3,309,182 A | 3/1967 | Crowley |
| 3,321,430 A | 5/1967 | Ott |
| 3,425,999 A | 2/1969 | Axelrood |
| 3,441,588 A | 4/1969 | Wagner |
| 3,531,527 A | 9/1970 | Tieh |
| 3,654,370 A | 4/1972 | Yeakey |
| 3,660,319 A | 5/1972 | Yeakey |
| 4,038,296 A | 7/1977 | Greif |
| 4,120,850 A | 10/1978 | Pechhold |
| 4,139,567 A | 2/1979 | Pruckmayr |
| 4,153,786 A | 5/1979 | Pruckmayr |
| 4,192,943 A | 3/1980 | Robinson |
| 4,198,464 A | 4/1980 | Login |
| 4,383,100 A | 5/1983 | Pechhold |
| 4,645,630 A | 2/1987 | Rasshofer |
| 4,658,065 A | 4/1987 | Aoshima |
| 4,742,168 A | 5/1988 | Zimmerman |
| 4,745,170 A | 5/1988 | Bushman |
| 4,747,851 A | 5/1988 | Sung |
| 4,847,417 A | 7/1989 | Larkin |
| 4,910,279 A | 3/1990 | Gillis |
| 4,919,878 A | 4/1990 | Pilger |
| 4,985,047 A | 1/1991 | Daly et al. |
| 5,011,647 A | 4/1991 | Meyer |
| 5,035,893 A | 7/1991 | Shioya |
| 5,093,383 A | 3/1992 | Cassidy |
| 5,104,959 A | 4/1992 | Hess |
| 5,126,424 A | 6/1992 | Brindopke |
| 5,183,876 A | 2/1993 | Kopp et al. |
| 5,183,877 A | 2/1993 | Swanson |
| 5,189,075 A | 2/1993 | Zimmerman |
| 5,364,909 A | 11/1994 | Guo |
| 5,407,453 A | 4/1995 | Pierce Ruhland |
| 5,558,684 A | 9/1996 | Derosa |
| 5,654,085 A | 8/1997 | Markusch |
| 5,752,991 A | 5/1998 | Plavac |
| 5,874,623 A | 2/1999 | Adkins |
| 5,892,130 A | 4/1999 | Van Voorst |
| 6,624,283 B2 | 9/2003 | Viegas et al. |
| 6,797,789 B2 | 9/2004 | Davis |
| 2002/0193550 A1 | 12/2002 | Nishikawa |
| 2004/0116594 A1 | 6/2004 | Bhattacharjee |
| 2006/0115531 A1 | 6/2006 | Chenault |
| 2007/0117949 A1 | 5/2007 | Palmer |
| 2007/0117953 A1 | 5/2007 | Palmer |
| 2009/0061172 A1 | 3/2009 | Hayashi |
| 2010/0021676 A1 | 1/2010 | Laubry |
| 2011/0174317 A1 | 7/2011 | Martin |

FOREIGN PATENT DOCUMENTS

| EP | 0282771 | 9/1988 |
| EP | 0499206 B1 | 7/1997 |
| JP | 2001234431 | 8/2001 |
| JP | 2001294838 | 10/2001 |
| JP | 2002348727 | 12/2002 |
| JP | 2002348730 | 12/2002 |
| JP | 2002363823 | 12/2002 |
| JP | 20046026979 | 1/2004 |
| WO | WO90/14327 | 11/1990 |
| WO | WO97/30103 | 8/1997 |
| WO | WO2011/071502 | 6/2011 |
| WO | WO2011/075177 | 6/2011 |

OTHER PUBLICATIONS

Su, et al., "Properties of polyurethane elastomers based on poly (oxyethylene-co-oxytetramethylene) diol", 2001 Chinese Journal of Polymer Science (English Edition) 19 (4), pp. 371-376 (Abstract).

Jordens, et al., "Novel creamer materials based on poly (propylene oxide) and tetramethoxsilane: Comparison of ACCLAIM™ polyether polyol and JEFFAMINE® and polyoxyalkyleneamine as the poly (propylene oxide) source", Journal of Macromolecular Science—Pure and Applied Chemistry, vol. 37A, Issue 3, Mar. 2000, pp. 177-203 (Abstract).

Lin, et al., "Synthesis and reactivity of Mannich-derived polyoxyethylene amines as epoxy curing agents", Dept. of Chemical Engineering, national Chung-Hsing University, Taichung 402, Taiwan (Abstract).

Iskender, et al., "Preparation of segmented, high molecular weight, aliphatic poly (ether-urea) copolymers in isopropanol. In-situ FTIR studies and polymer synthesis", Polymer, vol. 45, Issue 17, Aug. 5, 2004, pp. 5829-5836 (Abstract).

(Continued)

Primary Examiner — Duc Truong
(74) Attorney, Agent, or Firm — Robert B. Furr, Jr.

(57) ABSTRACT

Embodiments of the present disclosure include polyetheramines, methods of making polyetheramine, methods of using polyetheramine, and the like.

7 Claims, No Drawings

(56) References Cited

OTHER PUBLICATIONS

Van Der Hage, et al., "Structural Analysis of Polyoxyalkyleneamines by Matrix-Assisted Laser Desorption/Ionization on an External Ion Source FT-ICR-MS and NMR", Macromolecules, 1997, 30 (15), pp. 4302-4309 (Abstract).

Asai, et al., "Preparation and properties of imide-containing elastic polymers from elastic polyureas and pyromellitic dianhydride", Journal of Polymer Science Part A: Polymer Chemistry, vol. 38, Issue 4, pp. 715-723, Feb. 15, 2000 (Abstract).

"Synthesis and Characteristics of Epoxides", C. A. May and Y. Tanaka, Ed., Epoxy Resins Chemistry and Technology (Marcel Dekker, Inc.) [ Book—furnished upon request ].

Huntsman Technical Bulletin, JEFFAMINE® Amines as Curing Agents for Epoxy Resins in Composites.

POLYETHERAMINES, COMPOSITIONS INCLUDING POLYETHERAMINES, AND METHODS OF MAKING

CROSS-REFERENCE TO RELATED APPLICATION

This application claims priority to U.S. provisional application entitled "POLYETHERAMINES AND METHOD," having Ser. No. 61/381,453, filed on Sep. 10, 2010, which is entirely incorporated herein by reference.

BACKGROUND

Others have technology directed toward amine-terminated ethylene oxide (EO) tetrahydrofuran (THF) block copolymers, or block polyetheramines, prepared by ammonia displacement of terminal chlorine groups on block $\alpha,\omega$-dichloro polyalkylene oxide. However, that technology has significant disadvantages in that the preparation uses expensive reagents in the chlorination reaction, creates a chlorinated feed material and produces HCl as a by-product, which requires special handling, process equipment made from expensive materials of construction, and special treatment steps for by-product disposal. The technology also includes use of polyetheramines in the formation of block copolymers with adipic acid and hexamethylenediamine and the subsequent formation of polyamide fibers.

Other technologies mention the presence of greater than 3% secondary amine end groups in the copolymer for fiber applications.

Yet another technology relates to a poly(oxybutylene)poly(oxyethylene) diamine compound, as well as a use for the same as an additive to transportation motor fuels. Under some conditions, the use of 1,2-butylene oxide as a starting material can provide a branched segment in the co-polymer backbone after the amination step.

There remains a need for technology that overcomes and/or provides other advantages not present in previously disclosed technologies.

SUMMARY

Embodiments of the present disclosure include polyetheramines, methods of making polyetheramine, methods of using polyetheramine, and the like.

An embodiment of the present disclosure includes an $\alpha,\omega$-diamino poly(oxyethylene-co-oxytetramethylene ether) random copolymer composition having about 25 to about 75 mole % oxyethylene units.

An embodiment of a composition, among others, includes a polyetheramine composition according to the formula II:

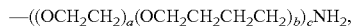
—((OCH$_2$CH$_2$)$_a$(OCH$_2$CH$_2$CH$_2$CH$_2$)$_b$)$_c$NH$_2$, wherein: a and b are each integers equal to or greater than 1; the ratio of a/b is from about 0.33 to about 3.0; c is an integer equal to or greater than 2; and the average value of c is from about 4 to about 26.

An embodiment of a method of preparing an $\alpha,\omega$-diamino poly(oxyethylene-co-oxytetramethylene ether) random copolymer composition, among others, includes the reductive amination of a poly(oxyethylene-co-oxytetramethylene ether) glycol in the presence of ammonia, hydrogen, and a reductive amination catalyst at an elevated temperature and elevated total pressure.

An embodiment of a method of preparing an $\alpha,\omega$-diamino poly(oxyethylene-co-oxytetramethylene ether) random copolymer composition, among others, includes: hydrogenating a poly(oxyethylene-co-oxytetramethylene ether) glycol at a temperature of about 150° C. to about 300° C. and a total pressure of about 1500 psig to about 4000 psig (about 10,400 kPa to about 27,700 kPa) in the presence of about 10:1 to about 150:1 molar ratio of ammonia to poly(oxyethylene-co-oxytetramethylene ether) glycol and a reductive amination catalyst to an $\alpha,\omega$-diamino poly(oxyethylene-co-oxytetramethylene ether) random copolymer; and recovering $\alpha,\omega$-diamino poly(oxyethylene-co-oxytetramethylene ether) random copolymer.

An embodiment of an epoxy resin curing agent, among others, includes an $\alpha,\omega$-diamino poly(oxyethylene-co-oxytetramethylene ether) random copolymer composition as described herein.

An embodiment of curing an epoxy resin curing agent, among others, includes contacting the epoxy resin with the polyetheramine as described herein.

An embodiment of curing a method of preparing a polyurea, among others, includes contacting a polyisocyanate with the polyetheramine as described herein.

DETAILED DESCRIPTION

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure employ, unless otherwise indicated, techniques of chemistry, and the like, which are within the skill of the art. Such techniques are explained fully in the literature.

Unless indicated otherwise: parts are parts by weight, concentration in % is % by weight, temperature is in ° C., and pressure is in atmospheres. Pressures reported in pounds per square inch gauge (psig) include the pressure of one atmosphere (14.7 pounds per square inch). One atmosphere is equivalent to 14.7 pounds per square inch absolute or 0 pounds per square inch gauge. Standard temperature and pressure are defined as 25° C. and 1 atmosphere.

It is to be understood that, unless otherwise indicated, the present disclosure is not limited to particular materials, reagents, reaction materials, manufacturing processes, or the like, as such can vary. It is also to be understood that the terminology used is for purposes of describing particular embodiments only, and is not intended to be limiting. It is also possible in the present disclosure that steps can be executed in different sequence where this is logically possible.

As used herein, for both the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure include polyetheramines, methods of making polyetheramine, methods of using polyetheramine, and the like. Embodiments of the present disclosure provide methods to prepare a polyetheramine, an amine-terminated ethylene oxide (EO) and tetrahydrofuran (THF) random copolymer, by a reductive amination of the glycol copolymer starting material with hydrogen and ammonia in contact with a suitable catalyst. The polyetheramine may have about 25 to about 75 mole % EO units and/or may have greater than 90% primary amine end groups. Unlike other technologies, polyetheramines of the present disclosure have very low secondary amine end groups (i.e., very high primary amine end groups) and would be desired for epoxy resin curing and for the preparation of polyureas and polyurethanes. In additions, other technologies do not use tetrahydrofuran (THF), where use of THF is advantageous in that it provides no branched segment in the co-polymer formed using THF. Furthermore, embodiments of the present disclosure provide a cost-effective method for the preparation of polyetheramines described herein.

An embodiment of the present disclosure includes a polyetheramine containing predominately unhindered primary amine ends that can impart lower viscosity to curing agent systems and increase flexibility and toughness when used in the curing, cross-linking, and hardening of epoxy resins.

In an embodiment, the polyetheramine has about 25 to about 75 mole % EO units and greater than 90% primary amine end groups. In an embodiment, the polyetheramine can be an α,ω-diamino poly(oxyethylene-co-oxytetramethylene ether) random copolymer composition having about 25 to about 75 mole % oxyethylene units.

Embodiments of the polyetheramines or poly(oxyethylene-co-oxytetramethylene ether) diamines, can be derived from the reductive amination of a random copolymer of ethylene oxide (EO) and tetrahydrofuran (THF). In an embodiment, the copolymers are a random poly(oxyethylene-co-oxytetramethylene ether) glycol and can be derived from the random copolymerization of ethylene oxide (EO) and tetrahydrofuran (THF).

In an embodiment, the poly(oxyethylene-co-oxytetramethylene ether) glycol can be represented structurally as Formula I:

$$H((OCH_2CH_2)_a(OCH_2CH_2CH_2CH_2)_b)_cOH$$

where, a and b can each independently be integers equal to or greater than 1, the ratio of a/b can be about 0.33 to about 3.0 and c can be an integer equal or greater than 2, and the average value of c can be about 4 to about 26. In an embodiment, the Formula I glycols can have a number average molecular weight of about 500 to about 3000 daltons, about 1000 to about 2500 daltons, or about 1500 to about 2500 daltons. In an embodiment, the Formula I glycols can have about 25 to about 75 mole % oxyethylene units, about 30 to about 65 mole % oxyethylene units, or about 40 to about 55 mole % oxyethylene units.

An embodiment of the polyetheramine is represented structurally as Formula II:

$$—(OCH_2CH_2)_a(OCH_2CH_2CH_2CH_2)_b)_cNH_2$$

where, a and b are each integers equal to or greater than 1, the ratio of a/b is from about 0.33 to about 3.0 and c is an integer equal or greater than 2, and the average value of c is from about 4 to about 26.

In an embodiment, polyetheramine diamine (Formula II polyetheramine or α,ω-diamino poly(oxyethylene-co-oxytetramethylene ether) random copolymer composition) may have a number average molecular weight of about 500 to about 3000 daltons or about 1000 to about 2500 daltons.

In an embodiment, the polyetheramine diamine (Formula II polyetheramine or α,ω-diamino poly(oxyethylene-co-oxytetramethylene ether) random copolymer composition) may have about 25 to about 75 mole % oxyethylene units, about 30 to about 65 mole %, or about 40 to about 55 mole %.

In an embodiment, the amine end groups of the polyetheramine diamine (Formula II polyetheramine or α,ω-diamino poly(oxyethylene-co-oxytetramethylene ether) random copolymer composition) may have, greater than about 85% primary amine groups, greater than about 90% primary amine groups, or greater than about 95% primary amine groups.

In an embodiment, the amine end groups of the polyetheramine diamine (Formula II polyetheramine or α,ω-diamino poly(oxyethylene-co-oxytetramethylene ether) random copolymer composition) may have amine end groups that are less than about 15% secondary amine groups, less than about 10% secondary amine groups, or less than about 5% secondary amine groups.

In an embodiment, the polyetheramine diamine (Formula II polyetheramine or α,ω-diamino poly(oxyethylene-co-oxytetramethylene ether) random copolymer composition) may have a polydispersity index of the random copolymer of about 1.5 to about 2.5 or about 1.8 to about 2.3.

In an embodiment, the polyetheramine diamine (Formula II polyetheramine or α,ω-diamino poly(oxyethylene-co-oxytetramethylene ether) random copolymer composition) may have a combination of the characteristics described above (e.g., number average molecular weight, mole % oxyethylene units, primary amine groups, amine end groups, and the polydispersity index of the random copolymer)

In some instances of the present disclosure, the Formula I glycol can be converted to polyetheramine (Formula II polyetheramine or α,ω-diamino poly(oxyethylene-co-oxytetramethylene ether) random copolymer composition) by reductive amination in the presence of ammonia, hydrogen, and a catalyst at an elevated temperature and pressure.

In an embodiment, the α,ω-diamino poly(oxyethylene-co-oxytetramethylene ether) random copolymer composition can be prepared by reductive amination of a poly(oxyethylene-co-oxytetramethylene ether) glycol in the presence of ammonia, hydrogen, and a reductive amination catalyst at an elevated temperature and elevated total pressure. In an embodiment, the molar ratio of ammonia to poly(oxyethylene-co-oxytetramethylene ether) glycol can be greater than the stoichiometric amount of ammonia required for complete conversion of hydroxyl ends to amine ends.

The reductive amination method is effectively carried out in a slurry catalyst system or in a fixed-bed system, where the latter can be operated in either a trickle bed or flooded bed mode.

Reductive amination catalysts can include cobalt or nickel catalysts, which may be present as supported catalysts, the support material may be silica, alumina, or silica-alumina, or as so-called skeletal metal catalysts, typified by Raney® type cobalt or nickel catalysts. The cobalt or nickel catalysts may also contain other metals, e.g. copper, chromium, or molybdenum, as promoters for the reductive amination reaction.

Sources of hydrogen can be molecular hydrogen, gas streams containing high concentrations of hydrogen (e.g., greater than about 80 mole % hydrogen), and gas mixtures containing hydrogen and other gaseous compounds that are inert in the reductive amination reaction, such as nitrogen, argon, or helium.

An excess of ammonia (above the molar equivalent required for complete conversion of hydroxyl ends to amine ends) is effective for promoting a high conversion of hydroxyl end groups and for a high selectivity for the formation of primary amines. The amount of ammonia can include a molar ratio of ammonia to starting polyether glycol of 10:1 or greater, for example about 30:1 to about 150:1, about 30:1 to about 100:1, or about 30:1 to about 60:1.

The conditions for reductive amination can include a temperature of about 150° C. to about 300° C. (e.g., about 170° C. to about 220° C. or about 190° C. to about 210° C.) and a total pressure (including vapor pressure of ammonia and hydrogen) of about 1500 psig to about 4000 psig (about 10,400 kPa to about 27,700 kPa) or about 2500 psig to about 3500 psig (about 17,235 kPa to about 24,132 kPa).

The amine-terminated EO-THF copolymers or polyetheramines of the present disclosure may be used as curing agents, cross-linkers, or hardeners, in the form of the neat polyetheramine, as blends with other amines, or as so-called adducts of the polyetheramine with an epoxy resin, where these amine curing agents are used to cure, cross-link, or harden epoxy resins whose applications include, for example, coatings, adhesives, or composites.

Blends of the polyetheramines of the present disclosure with other polyamines, for example amine-terminated polyoxypropylene glycols or for example triamines prepared by reaction of propylene oxide with a triol initiator, followed by amination of the terminal hydroxyl groups, are most desirable as these blends allow for balancing of process and performance properties in the final cured article.

In an embodiment, the polyetheramines of the present disclosure may contain unhindered di-primary amine groups, which may impart faster curing to the epoxy resin formulation than can be obtained by use of amine-terminated polyoxypropylene glycols, for example amine-terminated polypropylene glycols such as those sold under the trademark JEFFAMINE® D-series amines. The polyetheramines may impart lower viscosity to curing agent systems than those derived from amine-terminated polytetramethylene glycol curing agents, and may also provide a good balance of performance and processing properties, especially in composite applications, with increased flexibility, toughness and fracture resistance, while reducing crack propagation.

The amine curing agent can be combined with an epoxy resin, which is a polyepoxy compound containing about 2 or more 1,2-epoxy groups per molecule. Such epoxides are described in Y. Tanaka, "Synthesis and Characteristics of Epoxides", in C. A. May, Ed., *Epoxy Resins Chemistry and Technology* (Marcel Dekker 1988). Examples of commercially available epoxy resins include, but are not limited to, EPON® 825 (Hexion), EPON® 826 (Hexion), D.E.R.® 383 (Dow).

Other applications of the polyetheramines of the present disclosure can include their use in the preparation of polyureas and polyurethanes, particularly for use in RIM or spray processes, which may be used to prepare castings, coatings, adhesives or sealants.

Another application of the polyetheramines of the present disclosure include their use in the preparation of copoly(ether-amides) which, for example, may be used to prepare thermoplastic polyamide elastomers suitable for forming elastic shaped articles such as fibers with improved dyeability.

Poly(oxyalkylene) polyamines (also called polyetheramines or amine-terminated polyethers) have previously been reported as curing agents (hardeners, cross-linkers) for various epoxy resins in applications such as coatings, adhesives, and composites. See for example the Huntsman Technical Bulletin, *JEFFAMINE® Amines as Curing Agents for Epoxy Resins in Composites.*

The amine-terminated EO-THF copolymers of the present disclosure may be used as novel curing agents for epoxy resins, in the preparation of polyureas and polyurethanes, and in the preparation of copoly(ether-amides).

TEST METHODS

The amine-terminated EO-THF copolymers of the present disclosure are characterized by analytical techniques including titration of the amine end groups with standardized acids, for example using ASTM Test Method D2074-07 [2007; Standard Test Methods for Total, Primary, Secondary, and Tertiary Amine Values of Fatty Amines by Alternative Indicator Method].

The methods of IR spectroscopy and $^{13}$C NMR spectroscopy as known to the practitioner skilled in the art are used as needed.

Gas chromatography (GC) and proton NMR (nuclear magnetic resonance) are used to characterize and to analyze reaction products in the manner known to the skilled person.

All gas chromatographic (GC) analysis may be performed using an AGILENT TECHNOLOGIES 6890 equipped with AGILENT DB-5 or DB-1701 columns, helium (He) carrier gas, and flame ionization detectors.

All NMR analysis may be performed using a VARIAN, Inc. 500-MR (500 MHz magnet) or 600-MR (600 MHz magnet) spectrometer and software.

EXAMPLES

The following examples are put forth so as to provide those of ordinary skill in the art with a complete disclosure and description of how to perform the methods and use the compositions and compounds disclosed and claimed. Efforts have been made to ensure accuracy with respect to numbers (e.g., amounts, temperature, etc.), but some errors and deviations should be accounted for.

The following examples are provided to illustrate embodiments of the present disclosure. The examples are not intended to limit the scope of the present disclosure and should not be so interpreted.

Example 1

Preparation of Polyetheramine by Reductive Amination of an EO-THF Co-polymer, MW of about 2050

A 300 cc stirred autoclave is loaded with a mixture of 60.0 g of EO-THF (49 mole % EO) random co-polymer, MW=2060, and 10.0 g of Raney® 2724 cobalt catalyst, which is washed (with DI water until the wash water is neutral) and dried. The autoclave is purged with nitrogen, sealed, and 25 g ammonia is added to the autoclave. The stirrer is started and run at 1000 rpm, and hydrogen is added to the autoclave to give an initial internal pressure of about 650 psi gauge (psig) at room temperature. The autoclave is heated to 190° C. and hydrogen is added until the internal pressure of the autoclave is about 2500 psig. The mixture is stirred and heated for at least 7 hr., the autoclave is then cooled to room temperature, vented to atmospheric pressure, and 200 ml THF is added to dissolve the product. The product mixture is filtered to remove catalyst and the THF filtrate is stripped under vacuum to give the desired polyetheramine product. The polyetheramine product contains >90% primary amine end groups.

Example 2

Preparation of Polyetheramine by Reductive Amination of an EO-THF Co-polymer, MW of about 2050

A 300 cc stirred autoclave is loaded with a mixture of 50.0 g of EO-THF (49 mole % EO) random co-polymer, MW=2049, and 10.0 g of finely ground Johnson Matthey HTC Co 2000 cobalt catalyst, containing approximately 25% cobalt/cobalt oxide and approximately 75% aluminum oxide. The autoclave is purged with nitrogen, sealed, and 25 g ammonia is added to the autoclave. The stirrer is started and run at 1000 rpm, and hydrogen is added to the autoclave to give an initial internal pressure of about 650 psi gauge (psig) at room temperature. The autoclave is heated to 200° C. and hydrogen is added until the internal pressure of the autoclave is about 2500 psig. The mixture is stirred and heated for at least 8 hr., the autoclave is then cooled to room temperature, vented to atmospheric pressure, and 200 ml THF is added to dissolve the product. The product mixture is filtered to remove catalyst and the THF filtrate is stripped under vacuum to give the desired polyetheramine product. The polyetheramine product contains >90% primary amine end groups.

Example 3

Preparation of Polyetheramine by Reductive Amination of an EO-THF Co-polymer, MW of about 2500

A 300 cc stirred autoclave is loaded with a mixture of 60.0 g of EO-THF (37 mole % EO) random co-polymer, MW=2539, and 10.0 g of Raney® 2724 cobalt catalyst, which is washed (with DI water until the wash water is neutral) and dried. The autoclave is purged with nitrogen, sealed, and 25 g ammonia is added to the autoclave. The stirrer is started and run at 1000 rpm, and hydrogen is added to the autoclave to give an initial internal pressure of about 650 psig at room temperature. The autoclave is heated to 190° C. and hydrogen is added until the internal pressure of the autoclave is about 2500 psig. The mixture is stirred and heated for at least 7 hr., the autoclave is then cooled to room temperature, vented to atmospheric pressure, and 200 ml THF is added to dissolve the product. The product mixture is filtered to remove catalyst and the THF filtrate is stripped under vacuum to give the desired polyetheramine product. The polyetheramine product contains >90% primary amine end groups.

Example 4

Epoxy Resin Curing with Polyetheramine of Example 1, Blended with Commercial Curing Agent JEFFAMINE® T-403 Triamine (Huntsman)

6.2 g Polyetheramine, Example 1, Amine Hydrogen Equivalent Weight=515, is mixed with 46 g JEFFAMINE® T-403 triamine, Amine Hydrogen Equivalent Weight=81, and the amine curing agent blend is mixed with 100 g liquid epoxy resin, Epoxide Equivalent Weight=179, cast into a standard "dog bone" test sample and cured at 80° C. for two hours and 125° C. for three hours. The test sample shows improved flexural strength and increased fracture resistance compared to a test sample prepared by the same procedure using a comparative blend of JEFFAMINE® D-2000 diamine and JEFFAMINE® T-403 triamine curing agent.

While various aspects and embodiments have been disclosed, other aspects and embodiments will be apparent to those skilled in the art. The various aspects and embodiments disclosed are for purposes of illustration and are not intended to be limiting, with the true scope and spirit being indicated by the following claims.

It should be noted that ratios, concentrations, amounts, and other numerical data may be expressed in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±8%, or ±10%, of the numerical value(s) being modified. In addition, the phrase "about 'x' to 'y'" includes "about 'x' to about 'y'".

What is claimed is:

1. An $\alpha,\omega$-diamino poly(oxyethylene-co-oxytetramethylene ether) random copolymer composition comprising about 25 to about 75 mole % oxyethylene units.

2. The composition of claim 1, wherein the amine end groups comprise less than about 5% secondary amine groups.

3. The composition of claim 1, wherein the polydispersity index of the random copolymer is about 1.8 to about 2.3.

4. The composition of claim 1, wherein the composition has a number average molecular weight of about 500 to about 3000 daltons.

5. The composition of claim 4, wherein the composition has a number average molecular weight of about 100 to about 2500 daltons.

6. An epoxy resin curing agent comprising the $\alpha,\omega$-diamino poly(oxyethylene-co-oxytetramethylene ether) random copolymer composition of claim 1.

7. A method of curing an epoxy resin comprising contacting the epoxy resin with the polyetheramine of claim 2.

* * * * *